United States Patent
Junsheng

(12) 
(10) Patent No.: US 6,221,356 B1
(45) Date of Patent: *Apr. 24, 2001

(54) METHOD OF PREPARATION OF BIOLOGICALLY ACTIVE GINKGO BILOBA PRODUCT

(75) Inventor: Zhu Junsheng, Costa Mesa, CA (US)

(73) Assignee: Viva America Marketing, Inc., CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/764,932

(22) Filed: Dec. 13, 1996

(51) Int. Cl.$^7$ .................................................. A01N 65/00
(52) U.S. Cl. ............................................. 424/195.1
(58) Field of Search .......................................... 424/195.1

(56) References Cited

U.S. PATENT DOCUMENTS

| | | | |
|---|---|---|---|
| 5,389,370 | * | 2/1995 | O'Reilly et al. ................... 424/195.1 |
| 5,399,348 | * | 3/1995 | Scwabe ............................. 424/195.1 |
| 5,512,286 | * | 4/1996 | Schwabe ........................... 424/195.1 |

OTHER PUBLICATIONS

Kleijnen. J. and Knipschild, P., "Ginkgo Biloba for Cerebral Insufficiency"; *British Journal of Clinical Pharmacology*; 34:352–58 (1992).

DeFeudis, F.V. *Ginkgo Biloba Extract (EGb 761): Pharmacological Activities and Clinical Applications*; Editions Scientifiques Elsevier, Paris; 1: 1–8 (1991).

Kleijnen, J. and Knipschild, P., "Ginkgo Biloba", *The Lancet*, 340:1136–39 (1992).

Nakanishi K. et al, "The Ginkgolides. Isolation and Characterization of the Various Groups", *Tetrahedron Letters*, 4:299–302 (1967).

Clostre, F., "De l'organisme aux membranes cellulaires: les differents niveaux d'actions pharmacologiques de l'extrait de *Ginkgo biloba*", *La Presse Medicale*, 15:1529–1538 (Sep. 25, 1986).

Dreiu, K., "Preparation et definition de l'extrait de *Ginkgo biloba*", *La Presse Medical*, 15:1455–57 (Sep. 1986).

\* cited by examiner

*Primary Examiner*—L. Blaine Lankford
(74) *Attorney, Agent, or Firm*—Covington & Burling

(57) ABSTRACT

This invention provides a method for preparing a biologically active ginkgo biloba extract that is not subject to environmental restrictions and is efficient. The method involves extracting purified ginkgo biloba from ginkgo biloba leaf through a series of steps using alcohol as a solvent, including filtration, vacuum distillation, adsorption with silica gel, centrifugation, and chromatography. The invention also provides for a method of making dietary supplements from the ginkgo biloba product and of administering these supplements.

19 Claims, No Drawings

METHOD OF PREPARATION OF BIOLOGICALLY ACTIVE GINKGO BILOBA PRODUCT

BACKGROUND OF THE INVENTION

1. Field of the Invention

This invention relates to the field of human dietary supplements, and more specifically to improved supplements comprising extract preparations of the ginkgo biloba leaf, and to methods of making and administering such supplements.

2. Background

The ginkgo biloba tree is native to southeastern China, and is a member of the Ginkgoales family, which dates from the Permian Period of the Paleozoic Era. Ginkgo biloba has been a staple Chinese herbal ingredient for thousands of years, and is frequently recommended by Chinese herbal practitioners for coughs, asthma and acute allergic inflammations. Commercially prepared extracts of ginkgo biloba leaves have been used for decades as a medicinal aid, and are believed to be an important component of a food supplement program to ensure optimum nutritional health.

The commercially prepared mixtures are intended to substantially conform to an established molecular component profile, that includes a 24% flavonoid glycoside component, which comprises mostly kaempferol and quercetin glucorhamnoside esters, and 6% characteristic terpene lactones, the ginkgolides and bilobalides. A ratio of about 24% flavonoid glycosides to about 6% terpene lactones occurs in nature. [Kleijnen, J. and Knipschild, P., *Br. J. Pharmac.*, 34:352–58 (1992)].

This standardized ginkgo biloba extract comprised of a mixture of biologically active natural products provides for a complex range of activity. For example, the flavonoids present in ginkgo biloba function as free radical scavengers which reduce the amount of harmful free radicals in the body. Free radical formation can disrupt vascular membranes, resulting in increased microvascular permeability which in turn is associated with the impairment of cerebral blood flow seen with aging. Id. The terpene lactones present in ginkgo biloba, particularly ginkgolide B, are reported to be potent inhibitors of platelet-activating factor (PAF). [DeFeudis, F. G., *Ginkgo Biloba Extract (EGb 761), Pharmacological Activities and Clinical Applications* (Editions Scientifiques) (Elsevier, Paris (1991))]. PAF can disrupt vascular membranes, and is known to induce platelet aggregation, neutrophil degranulation, oxygen radical production, and bronchoconstriction. It has been reoirted that by its inhibition of PAF, ginkgolide B helps improve cerebral metabolism and protect the brain against hypoxic damage in laboratory animals with cerebral ischaemia. [Kleijnen, J. and Knipschild, P., *The Lancet* 340:1136–39 (1992)].

In addition to limiting membrane damage, ginkgo biloba extract appears to affect vascular tone, cerebral metabolism and neurotransmitters and their receptors. See DeFeudis, F. G., cited above. Ginkgo biloba extract is licensed in Germany for the treatment of cerebral dysfunction, hearing loss resulting from cervical syndrome, and peripheral arterial circulatory disturbances with intact circulatory reserve (intermittent claudication). See Kleijnen, J. and Knipschild, P., cited above. Other studies indicate the efficacy of using ginkgo biloba extract to improve mental acuity and memory enhancement. [Clostre, F., *La Presse Medicale*, 15: 1529–1538 (Sep. 25, 1986); Kleijnen, J., and Knipschild, P., cited above].

Flavonoid glycosides, which are part of the bioflavonoid family, are flavonoid molecules that are unique to ginkgo. The flavonoid glycosides include kaempferol, quercetin, sciadopitysin, luteolin, amentoflavone, isohamnetin, ginkgetin, delphidenon, isoginkgetin, procyanidin, bilobeitin, and prodelphinidin. Commercially available preparations of ginkgo also contains two other classes of chemical compounds, terpene lactones (ginkgolides A, B, C and bilobalide), and minor organic acids such as hydroxybenzoic acid, hydroxykynurenic acid, pyhrocathcuric acid and vanillic acid.

In addition to the medicinally beneficial compounds, potentially toxic components of the leaf, chiefly ginkgolic acid and ginkgol, are also present, but at non-toxic levels. These potentially toxic compounds belong to the ginkgolic acid family, and, regardless of their amount, are virtually eliminated by present-day commercial extraction processes.

3. Description of Prior Art

Total synthesis of the biologically active natural products of the ginkgo biloba leaf has been accomplished. [Nakanishi and Kishi, *Tet. Let.* 4:299–302 (1967)]. Due to the complexity of the molecular structure of these products, however, this synthesis is not cost-effective for production to meet present day consumer needs.

Commercially available ginkgo biloba extract has been prepared using an elaborate acetone-water extraction. [Drieu, K., *La Presse Medicale*, 15:1455–57 (September 1986)]. However, due to environmental regulations that severely restrict the use of acetone in the United States for food manufacturing purposes, the acetone-water methodology is acutely limited for commercial processes in the United States.

There is a need in the art for a means of producing ginkgo biloba product that is not subject to the regulatory restrictions and commercial expense that characterizes the current art.

SUMMARY OF THE INVENTION

The present invention relates to a novel method for preparing a non-toxic, highly biologically active product of ginkgo biloba, ginkgo biloba compositions produced by this method, nutritional supplements containing these compositions, and methods of administering these supplements. The novel method of the present invention comprises extracting the ginkgo biloba leaf using solvent systems that are free of toxic residues ginkgo biloba and that are safe to use on a manufacturing scale. The resulting product is a highly concentrated form of the active components of ginkgo biloba that is devoid of the unwanted and potentially toxic compounds of the ginkgolic acid family.

Therefore, an object of the present invention is to provide a useful method for preparing ginkgo biloba product.

Another object of the present invention is to provide an improved method for producing a highly biologically active ginkgo biloba product.

It is a further object of the present invention to provide a method of isolating ginkgo biloba products having high biological activity.

It is another object of the present invention to provide a method for the production of ginkgo biloba product that is safe for dietary supplementation to the human diet.

It is another object of the present invention to provide a form of ginkgo biloba product that is non-toxic to the human body.

It is another object of the present invention to provide methods of making nutritional supplements containing ginkgo biloba compositions.

It is still a further object of the present invention to provide nutritional supplements containing ginkgo biloba compositions.

It is yet another object of the present invention to provide methods of administering the nutritional supplements containing ginkgo biloba compositions.

It is a further object of the present invention to provide forms of ginkgo biloba product for use by the human body that increases the efficacy of certain memory enhancing cerebral metabolisms.

It is another object of the present invention to reduce the susceptibility of the human body to diminished mental capacities such as fatigue and lethargy, and to increase the efficacy of the human circulatory system, by administering the nutritional supplements of the invention.

BRIEF DESCRIPTION OF THE DRAWING

The accompanying drawings, which are incorporated in and constitute a part of this specification, illustrate particular embodiments of the invention, and together with the description, serve to explain the principles of the invention.

FIG. 1 is a flowchart illustrating a method of preparing a biologically active ginkgo biloba product according to the present invention.

FIG. 2 is a flowchart illustrating a method of preparing a biologically active ginkgo biloba product according to a particular embodiment of the invention described in Example 1.

FIG. 3 is a flowchart illustrating a method of preparing a biologically active ginkgo biloba product according to a particular embodiment of the invention described in Example 2.

FIG. 4 is a flowchart illustrating a method of preparing a biologically active ginkgo biloba product according to a particular embodiment of the invention described in Example 3.

DETAILED DESCRIPTION OF THE INVENTION

The present invention relates to certain methods of producing a highly biologically active product of ginkgo biloba in the form of a dried extract mass having an enriched content of ginkgolide A and ginkgolide B that possesses high biological activity. The present invention also relates to uses of the dried extract as a nutritional supplement for the human diet.

More particularly, the present invention includes a process for preparing biologically active ginkgo biloba extract comprising the steps of mixing ginkgo biloba and alcohol to form a solution, filtering the ginkgo biloba and alcohol solution to form a ginkgo biloba extract, and purifying the ginkgo biloba extract. The purifying step comprises adsorbing the ginkgo biloba extract. The filtering step may comprise partitioning the ginkgo biloba and alcohol solution with alcoholic solvent. The purifying step may also comprise centrifuging the ginkgo biloba extract, and may further comprise chromatographing the extract.

More particularly, the present invention in broad form includes a process for producing a ginkgo biloba product which comprises:

1. Mixing ginkgo biloba and alcohol to form a ginkgo biloba solution.
2. Extracting the ginkgo biloba solution to form a first ginkgo biloba filtrate.
3. Vacuum distilling the ginkgo biloba filtrate to form a ginkgo biloba slurry.
4. Filtering the ginkgo biloba slurry to form a second ginkgo biloba filtrate.
5. Adding an adsorbent to the second ginkgo biloba filtrate to form ginkgo biloba cake.
6. Washing the ginkgo biloba cake with alcohol and filtering to form a first ginkgo biloba liquor.
7. Vacuum distilling the first ginkgo biloba liquor to form a first ginkgo biloba solid.
8. Adding alcohol to the ginkgo biloba solid to form a second ginkgo biloba liquor.
9. Centrifuging the second ginkgo biloba liquor and decanting the ginkgo biloba supernatant.
10. Vacuum distilling the ginkgo biloba supernatant to yield a second ginkgo biloba solid.
11. Purifying the second ginkgo biloba solid through alcohol resuspension and chromatography to yield a purified ginkgo biloba extract;
12. Isolating a final dried ginkgo biloba product from the purified ginkgo biloba extract;

More specifically, with reference to the preferred embodiment depicted in FIG. 1, the process for preparing the ginkgo biloba dried product that has a high molecular content of ginkgolide A and ginkgolide B in a highly biologically active and non-toxic form comprises the following series of steps:

Mixing step (1) of contacting dried and pulverized ginkgo biloba leaves in an alcohol suspension yields a ginkgo biloba solution. A suitable form of ginkgo biloba is dried ginkgo biloba leaf that has been pulverized to form a fine powder. Dried ginkgo biloba leaf is commercially available from sources such as Starwest Botanicals, Rancho Cordova, Calif. Mixing step (1) preferably uses a 65–75% alcohol suspension, is conducted at a temperature from about 15° C. to 40° C., preferably 20° C. to 32° C., and uses about 1–2 parts ginkgo biloba leaf to about 2–12 parts alcohol, and preferably from about 1–2 parts ginkgo biloba dried leaf to about 2–10 parts alcohol, and most preferably about 1 part ginkgo biloba dried leaf to about 2 parts alcohol. The mixing step (1) preferably involves mixing with vigorous agitation about 30 minutes to about 24 hours, preferably 30 minutes to about 4 hours, and most preferably from about 30 minutes to about 2 hours. In this mixing step, and all subsequent steps, a preferred form of alcohol suspension is ethanol. The alcohol may contain other components, including distilled water and acetic acid.

Extracting step (2) yields a first ginkgo biloba filtrate. Extraction step (2) preferably comprises filtering the suspension using a relatively fine-pore filter (such as Whatman filter paper, #4) to yield a solid and a liquid filtrate. Extracting step (2) preferably comprises additional filtering steps, wherein the solid remaining after filtration is mixed with alcohol and the filtering step is repeated on this mixture. The extracting step (2) may comprise filtering in this manner from about 1 time to about 10 times, preferably from about 2 times to about 7 times, most preferably from about 3 to about 4 times. The liquid filtrates so obtained are then combined to form a single liquid filtrate. In a preferred embodiment, the first filtering step within extracting step (2) uses the 2000 ml alcohol from the initial alcohol suspension, and the subsequent filtering steps within extracting step (2) each use 1000 ml alcohol.

Vacuum distilling step (3) yields a slurry. Vacuum distilling step (3) uses a vacuum between about 0.1 mm Hg and about 25 mm Hg, preferably about 0.5 mm Hg to about 15 mm Hg, and most preferably about 5 mm Hg to about 10 mm Hg; at a temperature of about 25° C. to about 90° C., preferably about 35° C. to about 80° C., and most preferably between about 60° C. and about 70° C.

In filtering step (4) the ginkgo biloba slurry is filtered and washed with water. Filtering step (4) involves filtering the slurry using a wide-pore filter (such as glass wool) via gravity and washing with about 1–3 parts water to about 4–8 parts ginkgo biloba leaf powder (based on the initial weight of the ginkgo biloba leaf powder of about 300–700 grams, preferably about 400–600 grams, and most preferably about 500 grams), preferably about 1–3 parts water to about 3–6 parts ginkgo biloba leaf powder, and most preferably about 2 parts water to about 5 parts ginkgo biloba leaf powder to form a ginkgo biloba filtrate.

Adding adsorbent addition step (5) involves adding adsorbent to the ginkgo biloba filtrate to form a heterogeneous mixture in the form of a ginkgo biloba cake. The adsorbent employed in the present invention can be chosen from a number of adsorbent types. The preferred adsorbents are certain silicon dioxide polymers referred to as silica gels. The preferred silica gel will pass through a 260–400 mm mesh screen. A preferred silica is called silica gel 60. One variety of such is available from E. M. Merck Co. In a preferred embodiment, adding adsorbent step (5) uses about 0.5–3.0 parts silicon dioxide to about 0.5–3.0 parts ginkgo biloba filtrate, preferably about 0.5–2.0 parts silicon dioxide to about 0.5–3.0 parts ginkgo biloba filtrate, and most preferably about 1 part silicon dioxide to about 1 part ginkgo biloba filtrate.

In washing step (6), the heterogeneous ginkgo biloba cake is washed and filtered with alcohol and the resultant washes are combined to yield a first ginkgo biloba liquor. In a preferred embodiment, washing step (6) involves adding to the heterogeneous ginkgo biloba cake about 0.25–0.75 parts 75–90% alcohol to 1 part ginkgo biloba leaf powder (based on the mass of the initial ginkgo biloba leaf powder), and most preferably about 0.40 parts of 83% alcohol to about 1 part ginkgo biloba leaf powder, filtering with a relatively fine-pore filter, and then making three further washes involving additions and filtrations using about 0.1 to 0.5 parts 75–90% alcohol to about 1 part ginkgo biloba leaf powder, preferably about 0.1 to 0.4 parts 83% alcohol to about 1 part ginkgo biloba leaf powder, and most preferably about 0.2 parts 75–90% alcohol to about 1 part ginkgo biloba leaf powder. These washes when combined yield a first ginkgo biloba filtrate.

Vacuum distilling step (7) involves vacuum distilling the ginkgo biloba liquor to yield a first ginkgo biloba solid. Vacuum distilling step (7) is carried out at a vacuum between about 0.1 mm Hg and about 25 mm Hg, preferably about 0.5 mm Hg to about 15 mm Hg, and most preferably about 5 mm Hg to about 10 mm Hg; at a temperature of about 25° C. to about 90° C., preferably about 35° C. to about 80° C., and most preferably between about 60° C. and about 70° C.

In adding alcohol step (8) alcohol is added to the first ginkgo biloba solid to form a first ginkgo biloba liquor. Adding alcohol step (8) preferably uses 65–75% alcohol. In a preferred embodiment, adding alcohol step (8) further comprises adding sufficient alcohol to increase the final alcohol concentration of about 75% to about 90%.

Centrifuging step (9) comprises centrifuging the second ginkgo biloba liquor to form a pelletized biphasic mixture comprising pellets and a ginkgo biloba supernatant. Centrifuging step (9) also comprises decanting the ginkgo biloba supernatant. Centrifuging step (9) is performed at about 3000–5000 rpm, most preferably about 4000 rpm.

In vacuum distilling step (10), the ginkgo biloba supernatant is concentrated in vacuo for sufficient time to yield a second amorphous ginkgo biloba solid. Vacuum distillation step (10) is carried out at a vacuum between about 0.1 mm Hg and about 25 mm Hg, preferably about 0.5 mm Hg to about 15 mm Hg, and most preferably about 5 mm Hg to about 10 mm Hg; and at a temperature of about 25° C. to about 90° C., preferably about 35° C. to about 80° C., and most preferably between about 60° C. and about 70° C.

In purifying step (11) the second ginkgo biloba solid is resuspended in alcohol and chromatographed. Purifying step (11) involves adding a minimal amount of 75–90% alcohol to the second amorphous ginkgo biloba solid subjecting it to chromatography using medium pressure and a reverse phase C-18 adsorbent column. A final solid ginkgo biloba product may be isolated (12) from the purified ginkgo biloba extract.

In a preferred embodiment depicted in FIG. 1, in combining step (12), the purified ginkgo biloba extract may be then combined upon purification wherein the proper fractions yielded by the chromatography step in purifying step (11) are combined to form a homogeneous liquor which is a dilute alcoholic solution of the ginkgo biloba extract. In a preferred embodiment depicted in FIG. 1, this solution is then vacuum distilled in vacuum distilling step (13) to remove the alcohol and water to yield a final amorphous ginkgo biloba solid product. Vacuum distilling step (13) is preferably carried out at a vacuum between about 0.1 mm Hg and about 25 mm Hg, preferably about 0.5 mm Hg to about 15 mm Hg, and most preferably about 5 mm Hg to about 10 mm Hg, at a temperature of about 25° C. to about 90° C., preferably about 35° C. to about 80° C., and most preferably between about 60° C. and about 70° C.

The dried ginkgo biloba product obtained by this process may be used in nutritional supplements to improve the overall health. To prepare the nutritional supplements of the invention, the ginkgo biloba product of the present invention is blended in intimate admixture with a suitable carrier according to conventional compounding techniques. This carrier may take a wide variety of forms depending upon the form of preparation a desired for administration, e.g., oral, sublingual, nasal, or parenteral.

In preparing the nutritional supplements in oral dosage form, any of the usual media may be employed. For oral liquid preparations (e.g., suspensions, elixirs, and solutions), media containing for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, capsules, pills, tablets, and lozenges). Controlled release forms may also be used. Because of their ease in administration, tablets, pills, and capsules represent the most advantageous oral dosage unit form, in which case solid carriers are obviously employed. If desired, tablets may be sugar coated or enteric coated by standard techniques.

A preferred dosage of the present invention may consist of a lozenge for human oral consumption. The preferred weight of the lozenge is between about 500 mg to about 1000 mg, preferably about 700 mg. The ginkgo biloba lozenge may be taken up to 2–4 times a day. The total weight of one dosage of the present invention is between about 500 mg and about 1000 mg and most preferably about 700 mg. In a preferred embodiment, a dosage is administered twice daily.

The following example is illustrative only, and does not purport to limit the invention in any fashion.

EXAMPLE 1

Example 1 corresponds to the flowchart of FIG. 2. To 500 g of dried ginkgo biloba leaf [Starwest Botanicals, Rancho Cordova, Calif.] that had been freshly pulverized to a fine powder, was added 2 L of 70% ethanol, and the resultant suspension was stirred with vigor for approximately 1 hour. The mixture was then gravity filtered using a Whatman No. 4 filter. The resulting solid was then resuspended in 1 liter of 70% ethanol and this was stirred for one hour and filtered, and this process repeated two more times, for a total extract volume of 5 liters. The filtrates were combined and concentrated using a rotary evaporator under reduced pressure at ambient temperature of about 40° C. to give a slurry. This slurry was filtered using glass wool and washed with quantity sufficient water to bring the total volume to approximately 200 ml. To the filtrate was added 60 g of silica gel (260–400 mm mesh [E. M. Merck Co.]) to give a cake, and this was washed successively, about one half of an hour per washing, with 83% alcohol, initially using 200 mL followed by 3 washes each of 100 mL of 83% alcohol. The combined washings were concentrated using a rotary evaporator at ambient temperature to give a brown amorphous solid material. To this was added enough 70% alcohol to yield a homogeneous liquor (brown) and to this liquor was added a quantity sufficient of alcohol to bring the final concentration of alcohol in the liquor to 83%, which resulted in the formation of a precipitate. This heterogeneous mixture was centrifuged at 4,000 rpm for twenty minutes and then decanted. The liquor was then concentrated using a rotary evaporator to give an amorphous solid material as the crude product. This crude product was purified by chromatography using a gradient from 30% to 83% ethanol as eluent, medium pressure, and C-18 reverse phase silicon dioxide as an adsorbent.

EXAMPLE 2

Example 2 corresponds to the flowchart of FIG. 3. To a 4000 mL Erlenmeyer flask charged with 2000 mL of 70% ethanol, at ambient temperature and equipped with mechanical stirring device, was added 500 g of dried ginkgo biloba leaf [Starwest Botanicals, Rancho Cordova, Calif.] that had been freshly pulverized to a fine powder. The resulting brownish-green heterogeneous mixture was vigorously stirred for three hours, then gravity filtered through a Whatman #4 filter paper. The solid residue was resuspended in 750 ml of 70% alcohol, and this was stirred for 0.5 hr, then filtered similarly; and then additionally, this extraction and filtration process was twice carried out on the solid residue. The greenish-brown filtrate liquors were combined and concentrated in vacuo to give a viscous slurry. This was filtered through glass wool, and washed successively with small amounts of distilled water until the volume of the filtrate was 150 ml. To the filtrate was added 50 g of silica gel 60 [E. M. Merck Co. 360, 270–400] to form a cake, and to this was then added 150 mL of 80% ethanol, and the resulting suspension was stirred with vigor for about 30 minutes. This was filtered (gravity) and the solid material was resuspended in 50 mL of 80% ethanol and then stirred for 30 minutes. This extraction process using 50 mL of 80% ethanol was repeated two more times. The filtrates were combined and concentrated to dryness in vacuo (rotary evaporator, 1–3 mmHg) at between 35° C. and 45° C. The resulting solid was dissolved in 70% ethanol, and then to this was added enough ethanol to bring the final concentration of ethanol to 80%. This was then centrifuged at 4000 rpm for 20 min. The supernatant was separated and applied directly to a reverse phase C-18 medium pressure column packed with 80% ethanol, and this was eluted with a gradient of 30% to 83% ethanol. The fractions containing the active compounds were combined and then concentrated to dryness in vacuo (rotary evaporator).

EXAMPLE 3

Example 3 corresponds to the flowchart of FIG. 4. To a 4000 mL Erlenmeyer flask charged with 2000 mL of 70% ethanol with 1% acetic acid, at ambient temperature and equipped with mechanical stirring device was added 500 g of dried ginkgo biloba leaf that had been freshly pulverized to a fine powder. The resulting brownish-green heterogeneous mixture was vigorously stirred for three hours, then gravity filtered through a Whatman #4 filter paper. The solid residue was resuspended in 750 ml of 70% alcohol containing 1% acetic acid, and this was stirred for 0.5 hr, then filtered similarly; and then additionally, this extraction and filtration process was twice carried out on the solid residue. The greenish-brown filtrate liquors were combined and concentrated in vacuo to give a viscous slurry. This was filtered through glass wool, washing successively with small amounts of distilled water until the volume of the filtrate was 150 ml. To the filtrate was added 50 g of silica gel 60 [E. M. Merck Co. 360, 270–400] to form a cake, and to this was then added 150 mL of 80% ethanol, and the resulting suspension was stirred with vigor for about 30 minutes. This was filtered (gravity) and the solid material was resuspended in 50 mL of 80% ethanol and then stirred for 30 minutes. This extraction process using 50 ml of 80% ethanol was repeated twice, in addition. The filtrates were combined and concentrated to dryness in vacuo (rotary evaporator, 1–3 mm Hg) at between 35° C. and 45° C. The resulting solid was dissolved in 70% ethanol, and then to this was added enough ethanol to bring the final concentration of ethanol to 80%. This was then centrifuged at 4000 rpm for 20 min. The supernatant was separated and applied directly to a reverse phase C-18 medium pressure column packed with 80% ethanol, and this was eluted with a gradient of 30% to 83% ethanol. The fractions containing the active compounds were combined and then concentrated to dryness in vacuo (rotary evaporator).

Although particular embodiments of the invention have been described and illustrated herein, it is recognized that modifications and variations may readily occur to those skilled in the art, and consequently it is intended that the claims be interpreted to cover such modifications and equivalents.

We claim:

1. A process for preparing a biologically active ginkgo biloba extract in the absence of ketone solvents comprising the steps of
   (a) mixing ginkgo biloba and alcohol to form a ginkgo biloba solution;
   (b) filtering the ginkgo biloba solution to form a ginkgo biloba extract;
   (c) purifying the ginkgo biloba extract through reverse-phase chromatography to isolate the fractions of the ginkgo biloba extract containing active compounds and thereby yield a purified ginkgo biloba extract; and
   (d) isolating a dried ginkgo biloba product from the purified ginkgo biloba extract.

2. The process described in claim 1, wherein the filtering step comprises adding alcohol and filtering the ginkgo solution multiple times.

3. The process described in claim 1, wherein the purifying step further comprises centrifuging the ginkgo biloba extract.

4. The process described in claim 1, wherein the purifying step further comprises subjecting the ginkgo biloba extract to chromatography.

5. The process for preparing a biologically active ginkgo biloba extract in the absence of ketone solvents comprising the steps of (a) mixing ginkgo biloba and alcohol to form a ginkgo biloba solution;

(b) extracting the ginkgo biloba solution to form a first ginkgo biloba filtrate;

(c) vacuum distilling the ginkgo biloba filtrate to form a ginkgo biloba slurry;

(d) filtering the ginkgo biloba slurry to form a second ginkgo biloba filtrate;

(e) adding an adsorbent to the second ginkgo biloba filtrate to form a ginkgo biloba cake;

(f) washing the ginkgo biloba cake with alcohol and filtering to form a first ginkgo biloba liquor;

(g) vacuum distilling the first ginkgo biloba liquor to form a first ginkgo biloba solid;

(h) adding alcohol the ginkgo biloba solid to form a second ginkgo biloba liquor;

(i) centrifuging the second ginkgo biloba liquor and decanting the ginkgo biloba supernatant;

(j) vacuum distilling the ginkgo biloba supernatant to yield a second ginkgo biloba solid;

(k) purifying the second ginkgo biloba solid through alcohol resuspension and reverse-phase chromatography to isolate the fractions of the ginkgo biloba extract containing active compounds and thereby yield a purified ginkgo biloba extract; and (l) isolating a final dried ginkgo biloba product from the purified ginkgo biloba extract.

6. The process of claim 5, wherein the mixing step comprises mixing ginkgo biloba leaf and 65–75% alcohol in the ratio ranging from 1:2 to 1:12 ginkgo biloba to alcohol.

7. The process of claim 5, wherein the extracting step comprises filtering the ginkgo biloba solution through a fine pore filter from 1 to 10 times.

8. The process of claim 5, wherein the first vacuum distilling step comprises distilling in a vacuum from between 0.1 mm Hg and 25 mm Hg at a temperature between about 25° C. and about 90° C.

9. The process of claim 5, wherein the filtering step comprises filtering the ginkgo biloba slurry with a wide pore filter and washing with from about 1:8 to about 3:4 water:ginkgo biloba leaf powder.

10. The process of claim 5, wherein the first adding step comprises adding an adsorbent selected from the group consisting of silicon dioxide polymers.

11. The process of claim 5, wherein the washing step comprises washing the ginkgo biloba cake with four successive washes of alcohol.

12. The process of claim 5, wherein the second vacuum distilling step comprises distilling in a vacuum from about 0.1 mm Hg to about 25 mm Hg.

13. The process of claim 5, wherein the second addition step comprises adding from between about 65% to about 75% alcohol.

14. The process of claim 5, wherein the centrifuging step further comprises decanting the supernatant.

15. The process of claim 5, wherein the third vacuum distilling step comprises distilling in a vacuum from about 0.1 mm Hg to about 25 mm Hg.

16. The process of claim 5, wherein the purifying step comprises resuspending the second ginkgo biloba solid in 75–90% alcohol.

17. The process of claim 16, wherein the purifying step further comprises subjecting the resuspended second ginkgo biloba solid to chromatography.

18. The process of claim 5, wherein the isolating step comprises combining the fractions resulting from subjecting the resuspended second ginkgo biloba solid to chromatography and vacuum distilling the combined fractions to form a solid.

19. A nutritional supplement comprising the ginkgo biloba product prepared in accordance with the method of claim 1 in combination with a suitable carrier.

* * * * *